US010888676B2

(12) United States Patent
Buehler et al.

(10) Patent No.: US 10,888,676 B2
(45) Date of Patent: Jan. 12, 2021

(54) AEROSOL GENERATING SYSTEM WITH A RUPTURING SYSTEM FOR A CONTAINER

(71) Applicant: Philip Morris Products S.A., Neuchatel (CH)

(72) Inventors: Frederic Buehler, Neuchatel (CH); Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 682 days.

(21) Appl. No.: 15/320,458

(22) PCT Filed: Jun. 19, 2015

(86) PCT No.: PCT/EP2015/063883
§ 371 (c)(1),
(2) Date: Dec. 20, 2016

(87) PCT Pub. No.: WO2015/197502
PCT Pub. Date: Dec. 30, 2015

(65) Prior Publication Data
US 2018/0207376 A1    Jul. 26, 2018

(30) Foreign Application Priority Data

Jun. 23, 2014  (EP) ..................................... 14173558

(51) Int. Cl.
*A61M 15/00*  (2006.01)
*A61M 15/06*  (2006.01)
(Continued)

(52) U.S. Cl.
CPC ......... *A61M 15/0035* (2014.02); *A24F 40/48* (2020.01); *A24F 40/485* (2020.01);
(Continued)

(58) Field of Classification Search
USPC ....... 131/116, 353, 357, 369, 370, 188, 233, 131/363, 189, 350
See application file for complete search history.

(56) References Cited

U.S. PATENT DOCUMENTS

| 4,254,782 A | * | 3/1981 | Ligeti | ..................... A24F 13/04 |
| | | | | 131/187 |
| 6,085,745 A | * | 7/2000 | Levander | .......... A61M 15/0028 |
| | | | | 128/203.15 |

(Continued)

FOREIGN PATENT DOCUMENTS

| CN | 101141892 A | 3/2008 |
| CN | 201128665 Y | 10/2008 |

(Continued)

OTHER PUBLICATIONS

Office Action and Search Report dated Feb. 25, 2019 in the corresponding Chinese Application No. 201580030042.2 with English Translation 16 pages.

(Continued)

*Primary Examiner* — Michael J Felton
*Assistant Examiner* — Taryn Trace Willett
(74) *Attorney, Agent, or Firm* — Oblon, McClelland, Maier & Neustadt, L.L.P.

(57) ABSTRACT

An aerosol-generating system is provided, including a first container including at least one aerosol-generating substrate; a rupturing system including a first tube and a second tube, the first and second tubes being arranged in operational engagement defining a volume, wherein the first and second tubes are movable relative to each other along a first motion path from a first position to a second position, such that the defined volume is larger in the first position than in the second position, wherein the first tube includes a first rupturing member disposed at least partially inside the first tube, such that in the first position, the first rupturing (Continued)

member is contained completely in the defined volume of the first and second tubes, and wherein in the second position, the first rupturing member at least partially protrudes from the defined volume to rupture the container including said substrate.

16 Claims, 5 Drawing Sheets

(51) Int. Cl.
*A24F 40/485* (2020.01)
*A24F 40/48* (2020.01)
*A61M 11/04* (2006.01)

(52) U.S. Cl.
CPC ........ *A61M 15/0003* (2014.02); *A61M 15/06* (2013.01); *A61M 11/042* (2014.02)

(56) References Cited

U.S. PATENT DOCUMENTS

| | | | | |
|---|---|---|---|---|
| 7,798,152 | B1* | 9/2010 | Tannous | A24F 1/30 131/188 |
| 8,517,032 | B2* | 8/2013 | Urtsev | A24F 47/002 131/271 |
| 8,813,759 | B1* | 8/2014 | Horian | A61M 15/06 131/273 |
| 9,854,845 | B2* | 1/2018 | Plojoux | A24F 47/008 |
| 2008/0053465 | A1* | 3/2008 | Tarora | A24F 13/06 131/187 |
| 2009/0260641 | A1 | 10/2009 | Monsees et al. | |
| 2010/0186738 | A1* | 7/2010 | Kobayashi | A61M 15/0028 128/200.14 |
| 2012/0199663 | A1 | 8/2012 | Qiu | |
| 2012/0204889 | A1* | 8/2012 | Xiu | A24F 47/008 131/273 |
| 2012/0260928 | A1* | 10/2012 | Herholdt | A24D 3/048 131/335 |
| 2015/0040929 | A1* | 2/2015 | Hon | A24F 47/008 131/329 |
| 2015/0335064 | A1* | 11/2015 | Abisdid | A24D 1/08 131/350 |

FOREIGN PATENT DOCUMENTS

| | | | | |
|---|---|---|---|---|
| CN | 201330141 Y | | 10/2009 | |
| CN | 201878765 U | * | 6/2011 | ........... A24F 47/008 |
| CN | 202164090 U | | 3/2012 | |
| EP | 2 489 391 A1 | | 8/2012 | |
| JP | 2005-22706 A | | 1/2005 | |
| JP | 2009-45441 A | | 3/2009 | |
| WO | WO 2006/098171 A1 | | 9/2006 | |
| WO | 2007/090594 A1 | | 8/2007 | |
| WO | WO-2007090594 A1 | * | 8/2007 | ........... A24F 47/002 |

OTHER PUBLICATIONS

International Search Report and Written Opinion dated Sep. 25, 2015 in PCT/EP2015/063883 filed Jun. 19, 2015.
English translation of the combined Chinese Office Action and Search Report dated Oct. 31, 2019, in Patent Application No. 201580030042.2, 14 pages.
Japanese Office Action dated May 30, 2019 in Japanese Patent Application No. 2016-573913 (with English translation), 5 pages.
Japanese Office Action with English translation dated Jan. 30, 2020 in corresponding Japanese Patent Application No. 2016-573913, (7 pages).

* cited by examiner

AEROSOL GENERATING SYSTEM WITH A RUPTURING SYSTEM FOR A CONTAINER

The present invention relates to aerosol generating system with a piercing system for a container. The invention further relates to such a piercing system.

Aerosol generating devices often comprise a closed container with one or more aerosol generating agents like for example a flavourant like menthol or a nicotine containing substrate. In order to release the aerosol generating agent, the container needs to be broken or pierced.

One known system comprises an aerosol-generating device and a container containing the nicotine solution and the delivery enhancing compound. The device comprises an elongate piercing member configured to pierce one or more compartments of the container when it is inserted into the device. Such a system requires precise engineering of the piercing member to ensure both compartments are properly pierced. This increases the manufacturing complexity and costs, together with the risk of the piercing member failing after multiple uses.

Therefore, it is an object of the present invention to provide means for piercing containers for such aerosol-generating systems that is easy to operate and cost effective in production.

According to one aspect of the present invention, there is provided an aerosol-generating system comprising a first container comprising at least one aerosol-generating substrate, the aerosol-generating system further comprising a rupturing system. The rupturing system comprises: a first tube and a second tube, wherein the first tube and the second tube are arranged in operational engagement defining a volume, wherein the first tube and the second tube are movable relative to each other along a first motion path from a first position to a second position, such that the defined volume is larger in the first position than in the second position, wherein the first tube comprises a first rupturing member, arranged at least partially inside the first tube, such that in the first position, the first rupturing member is contained completely in the defined volume of the first tube and the second tube, and wherein in the second position, the first rupturing member at least partially protrudes from the defined volume to rupture the container comprising the at least one aerosol-generating substrate.

Arranging the system in a such a way enables the rupturing member to engage with the container coupled to the second tube only when the system is moved to the second position. On the other hand, the system is advantageous, as the rupturing system is entirely contained within the tubes in the first position. This allows for easy handling, as, for example no parts protrude from the rupturing system that may otherwise easily break off. Further, it may prevent injury to a consumer operating the system due to the enclosure of the rupturing elements. Further still, the handling of the system is improved over a system in which a consumer needs to align a container with a stationary, exposed piercing element, in particular, the risk of breaking off such a stationary, exposed piercing element is avoided.

As used herein, the term "operational engagement" refers to the first tube and the second tube being coupled together and movable relative to each other. Preferably, the first tube and the second tube are slidably movable relative to each other along the longitudinal axis.

The first rupturing member preferably comprises a distal end comprising a rupturing portion and a proximal end, wherein the first rupturing member is coupled to the first tube at the proximal end such that during movement of the first tube along the first motion path, the rupturing portion describes a second motion path that is at least partially not parallel to the first motion path.

The second tube comprises a guide member configured to guide the rupturing portion of the first rupturing member along the second motion path. The system is preferably configured such that the guide member comprises a cam surface; and the first rupturing member comprises a cam follower surface, such that during relative movement of the first tube and the second tube from the first position to the second position along the first motion path, the cam follower surface of the first rupturing element engages with the cam surface of the guide member to guide the rupturing portion of the first rupturing member along the second motion path. The use of a second motion path that is non-parallel to the first motion path allows for relative movement between the general axis of the tube and the rupturing member. This allows for a variety of different rupturing movements, like for example a sideways cutting movement.

Preferably, the cam surface comprises a linear portion and an arc portion, and the cam follower preferably comprises a corresponding linear portion and arc portion. Providing a linear portion on the cam surface and cam follower enables the second motion path to allow the rupturing portion to pierce the container before the arc portion of the cam and cam follower engages, at this point the arc portion of the cam and cam follower engages and introduces a progressive transverse movement to tear the container thus rupturing the container in a manner which allows air to flow through.

Where the second tube comprises a guide member, the guide member may be rotatable relative to the second tube about the proximal end. Providing such a guide member, configured to deflect away from the longitudinal axis of the rupturing system as the first tube and the second tube move along the first motion path, may enable an improved airflow through the rupturing system.

As used herein, the term "longitudinal" is used to describe the direction between the downstream or proximal end and the opposed upstream or distal end of the container and the term "transverse" is used to describe the direction perpendicular to the longitudinal direction.

The first rupturing member preferably has a distal end comprising a rupturing portion and a proximal end, the rupturing member being rotatable relative to the first tube about the proximal end. Where the guide member comprises a cam surface, and the first rupturing member comprises a cam follower surface, relative movement of the first tube and the second tube from the first position to the second position along the first motion path, causes the rupturing member to rotate about the proximal end, such that the rupturing portion follows the second motion path. Again, this allows for a variety of different rupturing movements, like for example a sideways cutting movement.

Providing a rupturing member which is rotatable about a proximal end thereof, enables the rupturing member to both pierce and tear a seal of a container, and thus rupture the seal. Therefore, the seal is broken more effectively and efficiently than with known systems. In particular, this allows for the creation of a hole that is bigger than the distal end of the rupturing member and thus may for example allow a fluid to flow through the hole, the fluid being for example gas or a liquid.

More preferably, the guide member is a second rupturing member, wherein in the second position, the second rupturing member at least partially protrudes from the volume into a second container. In the embodiment where the guide member is a second rupturing member, the second rupturing member comprises a distal end comprising a rupturing portion and a proximal end, wherein the second rupturing member is connected to the second tube at the proximal end such that during movement of the second tube along the first motion path, the rupturing portion describes a third motion path that is at least partially not parallel to the first motion path. This third motion path may be similar to the second rupturing path, but mirrored (as the first rupturing member and the second rupturing member typically move into opposite direction. Also the third motion path allows for relative movement between the longitudinal axis of the tube and the second rupturing member. This again allows for a variety of different rupturing movements, like for example a sideways cutting movement on the other side of the rupturing system.

In this way, the piercing system may be coupled to two containers to form a container having two sealed compartments. In the first position the distal end of the second tube rupturing member is preferably contained completely in the defined volume of the first tube and the second tube, and wherein in the second position, the second rupturing member at least partially protrudes from the defined volume.

The first rupturing member is preferably coupled to the first tube by a resilient member. The resilient member is preferably configured to deform when the guide member of the second tube acts on the first rupturing member of the first tube. The resilient member and the rupturing member are arranged such that the rupturing member rotates about an axis transverse to the longitudinal axis of the piercing system.

Preferably, the rupturing portion or each rupturing portion has a wedge shaped longitudinal cross-section. One side of the wedge shape may be substantially parallel to the longitudinal axis of the system when the rupturing system is in the first position. In this way, the rupturing system may create a hole within a seal of a container more effectively. In a preferred embodiment, the rupturing portion first pierces a seal before the cam follower surface engages with the cam surface, as the system is moved from this intermediate position to the second position, the follower surface engages with the cam surface and provides for a transverse component of movement of the rupturing portion. The combination of the longitudinal, and transverse movement of the piercing portion breaks the seal of a container and opens the formed hole to enable an airflow pathway to be formed when in use.

Preferably, the rupturing portion or each rupturing portion has a transverse cross-sectional shape such that a flow path is formed between the inside of the container and the outside of the container, through the rupturing portion. For example, the transverse cross-sectional shape may be v-shaped, u-shaped, or the like. Alternatively, the rupturing portion may be at least partially hollow along its longitudinal length.

In a preferred embodiment, the first tube and the second tube are substantially hollow, wherein the external surface of the first tube is configured to slide adjacent the internal surface of the second tube. The external surface of the first tube and the internal surface of the second tube preferably each comprise resilient protrusions configured to cooperate to retain the system in the first position until a longitudinal compressive force is applied to the system. Such resilient protrusions prevent accidental use of the system.

The resilient protrusions are preferably annular rings extending about the respective surfaces of the first tube and the second tube. The annular rings preferably have a hemispherical cross-sectional shape.

Similarly, the external surface of the first tube and the internal surface of the second tube may each comprise resilient protrusions configured to cooperate to retain the system in the second position. Again, the resilient protrusions are preferably annular rings extending about the respective surfaces of the first tube and the second tube. The annular rings preferably have a hemispherical cross-sectional shape.

The hollow cylinder of the first shell may comprise a shoulder. As such, the system further comprises a removable tab positioned adjacent the shoulder and adjacent the end face of the second shell to prevent the system moving from the first position to the second position. Such a removable tab prevents use of the piercing system even if a longitudinal force is applied to the system. The removable tab is preferably removably coupled to at least one of the first shell shoulder and the end face of the second shell. The removable tab is preferably removably coupled using a plurality of frangible couplings. Alternatively, the removable tab may comprise a ring, free to rotate about the piercing system, having a frangible portion to enable the ring to be separated from the piercing system.

As will be appreciated, the removable tab is removed prior to use of the system.

The first container preferably comprises a first closed compartment comprising the aerosol-generating substrate, the compartment having at least one frangible barrier, and wherein the one frangible barrier defines a border of the volume. The frangible barrier is preferably directly adjacent an end face of the second tube. Preferably, the frangible barrier is sealed to the end face of the second tube.

The system may further comprise a second container, wherein the second container comprises a closed second compartment, the compartment having at least one frangible barrier and wherein the one frangible barrier defines a portion of the volume. The frangible barrier of the second compartment is preferably directly adjacent an end face of the first tube. Preferably, the frangible barrier is sealed to the end face of the first tube.

The aerosol-generating system may further comprise: at least one further rupturing system; and a mouthpiece element directly coupled to the second tube of the at least one further rupturing system.

An aerosol-generating system according to any of the preceding claims, further comprising at least one heater configured to heat the aerosol-generating substrate to form an aerosol.

The container of the aerosol-generating system may comprise any form of suitable aerosol-generating substrate. For example, the substrate may be a gas, a liquid, or a solid in the form of a powder. The aerosol-generating substrate may be volatile such that upon rupturing the container an aerosol is formed which may be inhaled by a user.

The first rupturing portion may comprise a capillary wick for wicking the liquid contents of the container. In this example, the aerosol is formed as the liquid evaporates from the capillary wick, for example as the user draws on the system. Preferably, to increase the evaporation rate of the liquid from the wick, a heater is provided adjacent the end of the capillary wick. The heater may be an electrical heater, such as a resistance heater, or an induction heater.

According to a further aspect of the present invention, there is provided a rupturing system. The rupturing system comprises: a first tube and a second tube, wherein the first tube and the second tube are arranged in operational engagement defining a volume, wherein the first tube and the second tube are movable relative to each other along a first motion path from a first position to a second position, such that the defined volume is larger in the first position than in the second position, wherein the first tube comprises a first rupturing member, arranged at least partially inside the first tube, such that in the first position, the first rupturing member is contained completely in the defined volume of the first tube and the second tube, and wherein in the second position, the first rupturing member at least partially protrudes from the defined volume to rupture a container.

As will be appreciated, where appropriate, any of the features described with reference to the rupturing system as being part of the aerosol-generating system are also applicable to the rupturing system as described as an independent system.

Such a rupturing system is configured to be coupled to a container comprising a liquid as described herein. Providing such a rupturing system reduces the requirement to provide aerosol-generating devices, systems, and the like, with an elongate piercing member and thus reduces the requirement for precise engineering along with reducing the associated complexities and costs.

According to a further aspect of the present invention, there is provided a container comprising a liquid nicotine composition, for use in an aerosol-generating device. The container comprises: a sealed compartment comprising the liquid nicotine composition, the compartment having at least one frangible barrier; and a rupturing system as described herein. The second tube of the rupturing system is directly coupled to the compartment adjacent the frangible barrier, such that when the first tube and the second tube are slidably moved relative to each other the rupturing member pierces and tears the frangible barrier as the distal end of the rupturing member moves along the second motion path and into the frangible barrier.

The container may further comprise a further sealed compartment comprising a delivery enhancing compound. The further sealed compartment being directly coupled to the first tube In this embodiment, the rupturing system comprises a guide member having a rupturing portion as described above. The rupturing system is provided between the sealed compartments, such that, in use, when the user applies a longitudinal compressive force to the container, the rupturing system moves from the first position to the second position, thereby piercing and tearing the seals of each compartment.

The container may comprise at a mouthpiece element directly coupled to a first tube of the rupturing system. In this embodiment, the first tube of the rupturing system does not comprise a rupturing portion.

In a particularly preferred embodiment, the container comprises: a first compartment comprising liquid nicotine composition and having first and second frangible barriers, a second compartment comprising the delivery enhancing compound and having third and fourth frangible barriers, a first rupturing system having first and second rupturing portions, positioned between the first and second compartments, a mouthpiece element and a second rupturing system having a first rupturing portion and a guide member positioned between the second compartment and the mouthpiece.

In use, the user applies a longitudinal compressive force to the container which moves the first and second rupturing systems from the first position to the second position which in turn pieces the second, third and fourth frangible barriers. The first frangible barrier being pierced when the container is inserted into an aerosol-generating device as described below.

Preferably, each frangible barrier is made from metal film, and more preferably from aluminium film.

As used herein, the terms 'upstream', 'downstream' and 'distal' and 'proximal' are used to describe the relative positions of components, or portions of components, of containers, aerosol-generating devices and aerosol-generating systems according to the invention in relation to the direction of air drawn through the containers, aerosol-generating devices and aerosol-generating systems during use thereof. It will be understood that the terms 'distal' and 'proximal', when used to describe the relative positions of other components, are used such that the distal end is the 'free' end and the proximal end is the 'fixed' end.

The delivery enhancing compound, where present, is preferably sorbed on a tubular porous element with a compartment. As used herein, by "sorbed" it is meant that the delivery enhancing compound is adsorbed on the surface of the tubular porous element, or absorbed in the tubular porous element, or both adsorbed on and absorbed in the tubular porous element.

The volume of the first compartment and the second compartment may be the same or different. In a preferred embodiment, the volume of the second compartment is greater than the volume of the first compartment.

The mouthpiece, where present, may comprise any suitable material or combination of materials. Examples of suitable materials include thermoplastics that are suitable for food or pharmaceutical applications, for example polypropylene, polyetheretherketone (PEEK) and polyethylene.

According to a yet further aspect of the present invention, there is provided an aerosol-generating system comprising an aerosol-generating device and a container as described herein. The aerosol-generating device comprises: an outer housing adapted to receive the container, and comprising at least one air inlet; and a piercing member for piercing an upstream frangible barrier of the container. The upstream seal being the first frangible barrier of the particularly preferred embodiment of the container described above. The elongate piercing member comprises: a piercing portion at a distal end of the piercing member. When the container is received in the aerosol-generating device, the at least one air inlet is in fluid communication with the container.

The piercing member is preferably positioned within the outer housing along the central longitudinal axis of the aerosol-generating device.

As used herein, the term "aerosol-generating device" refers to an aerosol-generating device that interacts with an aerosol-generating article to generate an aerosol that is directly inhalable into a user's lungs thorough the user's mouth.

As used herein, the term "air inlet" is used to describe one or more apertures through which air may be drawn into the aerosol-generating system.

In the particularly preferred embodiments, the first compartment and the second compartment are arranged in series from air inlet to the mouthpiece within the aerosol-generating system. That is, the first compartment is downstream of the air inlet, the second compartment is downstream of the first compartment and the air outlet is downstream of the second compartment. In use, a stream of air is drawn into the aerosol-generating system through the air inlet, downstream through the first compartment and the second compartment and out of the aerosol-generating system through the mouthpiece.

As used herein, by "series" it is meant that the first compartment and the second compartment are arranged within the aerosol-generating article so that in use an air stream drawn through the aerosol-generating article passes through the first compartment and then passes through the second compartment. Delivery enhancing compound vapour is released from the delivery enhancing compound in a compartment into the air stream drawn through the container and volatile nicotine liquid vapour is released from a compartment into the air stream drawn through container. The delivery enhancing compound vapour reacts with the volatile nicotine liquid vapour in the gas phase to form an aerosol, which is delivered to a user.

In a preferred embodiment a piercing portion of the aerosol-generating device piercing member is conical. However, it should be understood that the piercing portion may be of any shape suitable for piercing the compartments of the aerosol-generating article. Where the piercing portion is conical, the maximum diameter of the piercing portion corresponds to the diameter of the base circle of the cone.

In a preferred embodiment the outer housing of the aerosol-generating device comprises a cavity configured to receive the aerosol-generating article. Preferably, the cavity has a longitudinal length greater than the longitudinal length of the elongate piercing member. In this way, the piercing portion of the piercing member is not exposed, or accessible by the user.

Preferably, the cavity of the aerosol-generating device is substantially cylindrical. The cavity of the aerosol-generating device may have a transverse cross-section of any suitable shape. For example, the cavity may be of substantially circular, elliptical, triangular, square, rhomboidal, trapezoidal, pentagonal, hexagonal or octagonal transverse cross-section.

Preferably, the cavity of the aerosol-generating device has a transverse cross-section of substantially the same shape as the transverse cross-section of the container to be received in the cavity.

The overall dimensions of the aerosol-generating system may be similar to a conventional smoking article such as a cigarette, a cigar a cigarillo or any other such smoking article.

The delivery enhancing compound may comprise an organic acid or an inorganic acid. Preferably, the delivery enhancing compound comprises an organic acid. More preferably, the delivery enhancing compound comprises a carboxylic acid. Most preferably, the delivery enhancing compound comprises an alpha-hydroxy, an alpha-keto or 2-oxo acid.

In a preferred embodiment, the delivery enhancing compound comprises an acid selected from the group consisting of lactic acid, 3-methyl-2-oxovaleric acid, pyruvic acid, 2-oxovaleric acid, 4-methyl-2-oxovaleric acid, 3-methyl-2-oxobutanoic acid, 2-oxooctanoic acid and combinations thereof. In a particularly preferred embodiment, the delivery enhancing compound comprises pyruvic acid.

Preferably, the liquid within the container preferably comprises one or more of nicotine, nicotine base, a nicotine salt, or a nicotine derivative. Alternatively, the container may comprise a flavourant, such as for example, menthol.

The source of nicotine may comprise natural nicotine or synthetic nicotine. The source of nicotine may comprise nicotine base, a nicotine salt, such as nicotine-HCl, nicotine-bitartrate, or nicotine-ditartrate, or a combination thereof.

Alternatively or in addition, the source of nicotine may further comprise other components including, but not limited to, natural flavours, artificial flavours and antioxidants.

Preferably, the container comprises a liquid nicotine formulation.

The invention allows a cost effective, compact and easy to use aerosol-generating system to be provided. Furthermore, by using an acid or ammonium chloride as a delivery enhancing agent in aerosol-generating articles according to the invention, the pharmacokinetic rate of the nicotine may be advantageously increased.

Preferably, the container comprises an opaque outer housing. This advantageously reduces the risk of degradation of the acid or ammonium chloride and nicotine formulation due to exposure to light.

Preferably, the container is not refillable. Thus, when the nicotine formulation has been used up, the container is replaced, along with the piercing system. Thus, the piercing system is not required to be as robust as the known systems reducing the associated costs.

Advantageously, all elements of the device which are potentially in contact with the acid or ammonium chloride or the source of nicotine are changed when the container is replaced. This avoids any cross-contamination in the device between different mouthpieces and different containers, for example containers comprising different acids or sources of nicotine.

The nicotine formulation may be advantageously protected from exposure to oxygen (because oxygen cannot generally pass through the frangible barrier until it is pierced by the piercing member) and in some embodiments light, so that the risk of degradation of the nicotine formulation is significantly reduced. Therefore, a high level of hygiene can be maintained.

The container may have a transverse cross-section of any suitable shape. Preferably, the container is of substantially circular transverse cross-section or of substantially elliptical transverse cross-section. More preferably, the container is of substantially circular transverse cross-section.

Preferably, the container has a transverse cross-section substantially the same shape as the cavity of the aerosol-generating device.

The outer housing of the device may be formed from any suitable material or combination of materials. Examples of suitable materials include, but are not limited to, metals, alloys, plastics or composite materials containing one or more of those materials. Preferably, the outer housing is light and non-brittle.

The aerosol-generating system and device are preferably portable. The aerosol-generating system may have a size and shape comparable to a conventional smoking article, such as a cigar or cigarette.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention will be further described, by way of example only, with reference to the accompanying drawings in which.

Figure 1:
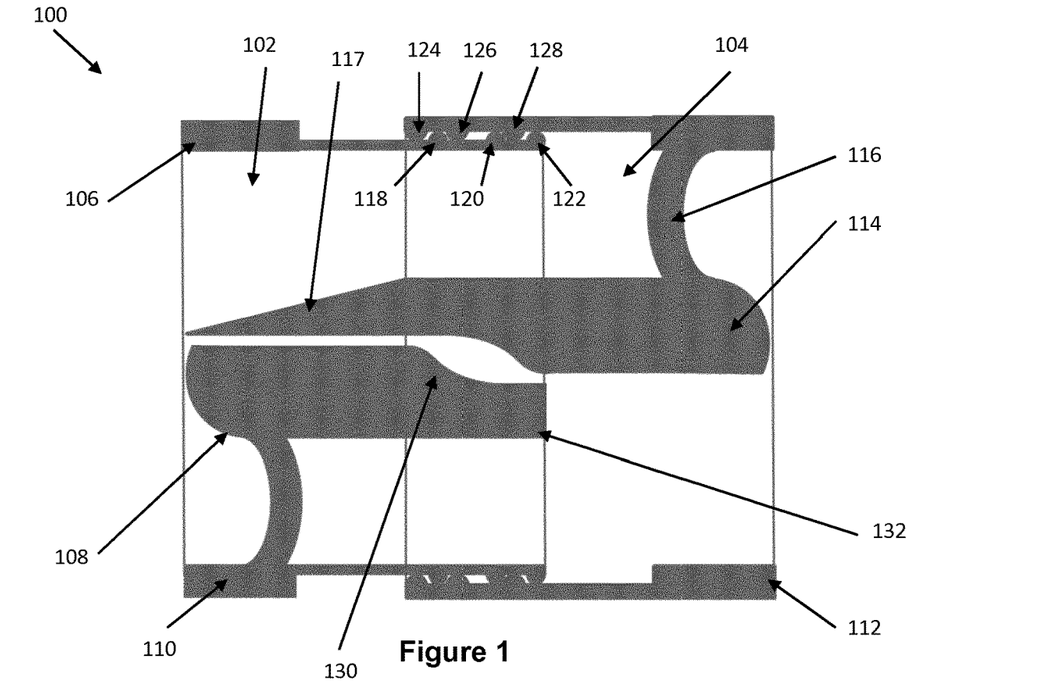
FIG. 1 shows a cross-sectional view of a piercing system according to the present invention.

FIG. 1 shows a cross-sectional view of a rupturing system 100 comprising a first tube 102 and a second tube 104. The first tube comprises a hollow cylindrical portion 106 having a substantially circular cross-sectional shape, and a guide member 108 resiliently coupled to the hollow portion 106 by the resilient member 110. The second tube 104 comprises a hollow cylindrical portion 112 having a substantially circular cross-sectional shape, and a rupturing member 114 resiliently coupled to the hollow portion 112 by the resilient member 116. The rupturing member comprises a rupturing portion 117. The first tube 102 further comprises resilient protrusions 118, 120 and 122, and the second tube 104 further comprises resilient protrusions 124, 126 and 128.

As can be seen in FIG. 1, the first tube 102 is configured to partially slide within the second tube 104, such that they are in operational engagement, as described in detail below. The first tube and the second tube are configured to move along a first motion path. Such relative sliding of the first tube 102 and the second tube 104 engages a cam surface 130 of the guide member 108 with a cam follower surface 132 of the rupturing member 114, as described in detail below.

Figure 2:
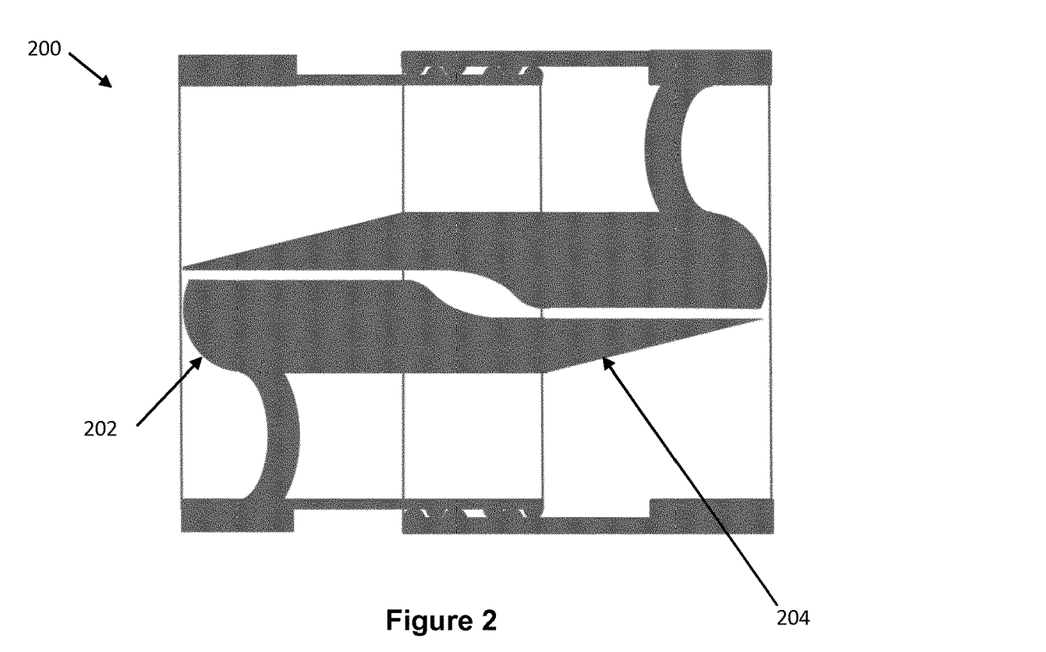
FIG. 2 shows a cross-sectional view of an alternative piercing system according to the present invention.

FIG. 2 shows an alternative rupturing system 200. As can be seen, the system 200 is similar to the system 100, and like reference numerals have been used to refer to like components. The first tube 102 of the system 200 comprises a guide member 202 having a rupturing portion 204. In this example, the guide member 202 is known as a second rupturing member.

Figure 3A:
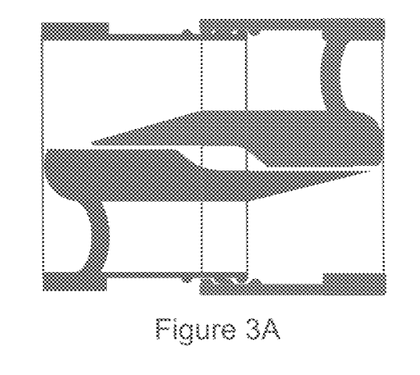
FIGS. 3A-3C show the piercing system of FIG. 2 moving from a first position to a second position.
Figure 3B:
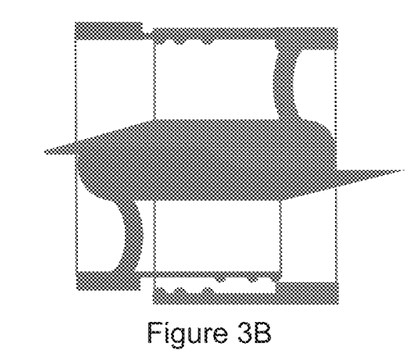
Figure 3C:
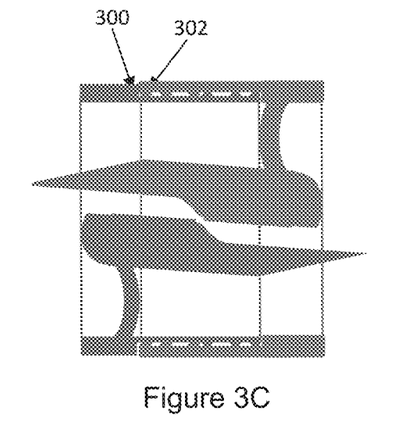

FIGS. 3A-3C show the rupturing system 200 moving from a first position, FIG. 3A, to an intermediate position, FIG. 3B, to a second position FIG. 3C, along the first motion path. As will be appreciated, the operation of the rupturing system 100 is substantially similar to that of system 200.

In FIG. 3A it can be seen that the protrusions 114, 120 and 122 of the first tube 102 cooperate with the protrusions 124, 126 and 128 of the second tube 104 to retain the first and second tubes in this first position until a longitudinal compressive force is applied to the system 200. Once sufficient force is applied, the first tube and the protrusions deform to allow the first tube to slide within the second tube, as shown in FIG. 3B. As can also be seen in FIG. 3B, the respective rupturing portions of the first tube and second tube protrude from the ends of the rupturing system. At the same time, the cam surface 130 begins to engage with the cam follower surface 132. As the first tube and second tube are moved to the second position as shown in FIG. 3C, the cam surfaces force the cam member 202 and the rupturing member 114 to rotate about their respective resilient members 110 and 116. In doing so, the rupturing portions move in the transverse direction, and thus the rupturing portions move along a second motion path, the second motion path not being parallel to the first motion path.

Finally, as can be seen in FIG. 3C, the resilient protrusions 118 and 128 cooperate to retain the system 200 in the second position. In addition, the first tube comprises a shoulder 300 which engages with an end face 302 of the second tube.

In FIG. 3(a) it can be seen that the protrusions 118, 120 and 122 of the first tube 102 cooperate with the protrusions 124, 126 and 128 of the second tube 104 to retain the first and second tubes in this first position until a longitudinal compressive force is applied to the system 200. Once sufficient force is applied, the first tube and the protrusions deform to allow the first tube to slide within the second tube, as shown in FIG. 3(b). As can also be seen in FIG. 3(b) the respective rupturing portions of the first tube and second tube protrude from the ends of the rupturing system. At the same time, the cam surface 130 begins to engage with the cam follower surface 132. As the first tube and second tube are moved to the second position as shown in FIG. 3(c) the cam surfaces force the cam member 202 and the rupturing member 114 to rotate about their respective resilient members 110 and 116. In doing so, the rupturing portions move in the transverse direction, and thus the rupturing portions move along a second motion path, the second motion path not being parallel to the first motion path.

Finally, as can be seen in FIG. 3(c), the resilient protrusions 118 and 128 cooperate to retain the system 200 in the second position. In addition, the first tube comprises a shoulder 300 which engages with an end face 302 of the second tube.

Figure 4:
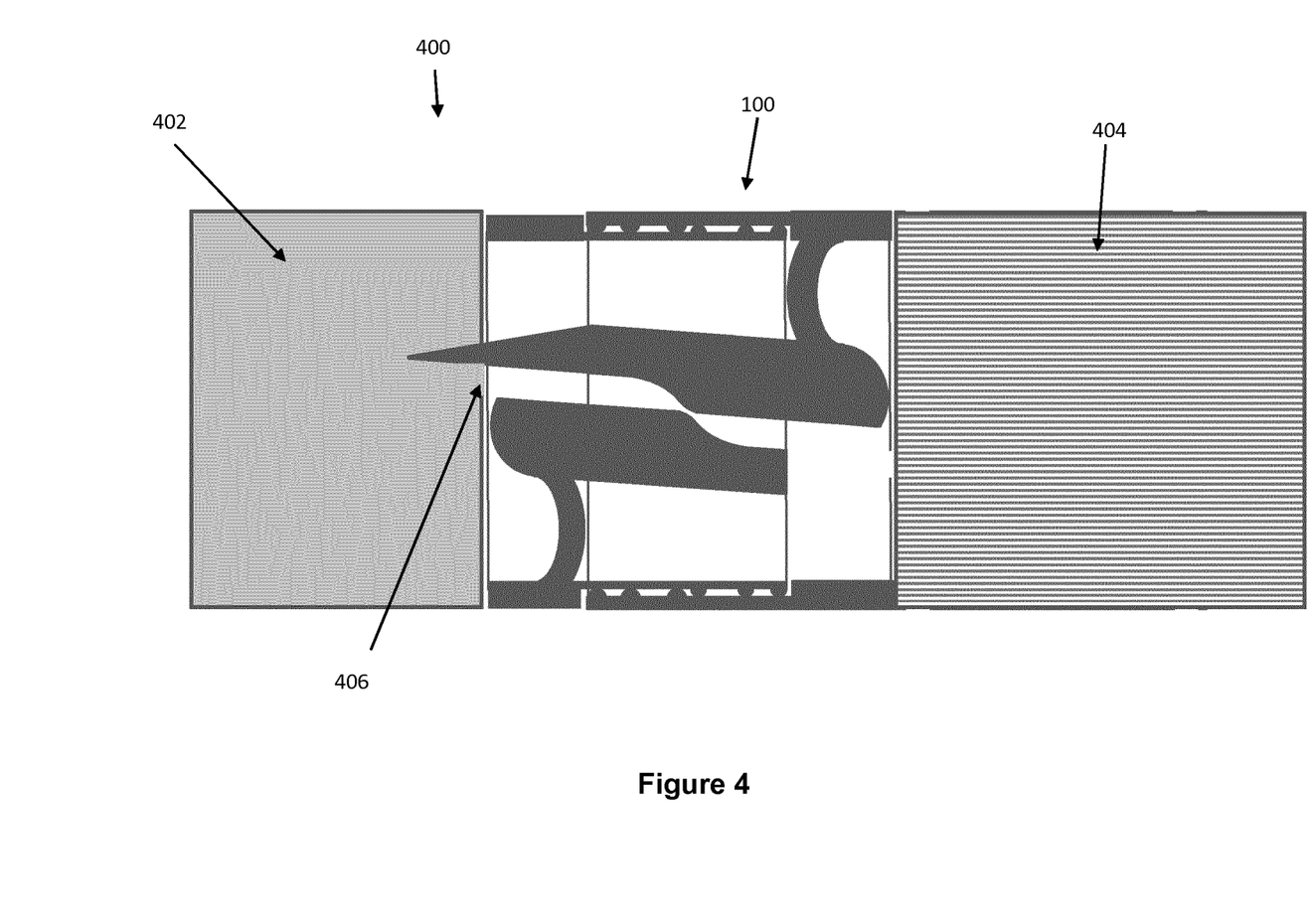
FIG. 4 shows a cross-sectional view of a container according to the present invention.

FIG. 4 shows a cross-sectional view of a container 400 comprising a rupturing system 100 as described above. The container further comprises a sealed compartment 402 comprising a volatile nicotine liquid source. The compartment 402 is coupled to the first tube 102. The container further comprises a mouthpiece portion 404 coupled to the second tube 104. As can be seen, the rupturing system 100 is in the second position, in which the rupturing member has ruptured the sealed compartment 402 and torn a hole 406 as the rupturing member 114 is forced in a transverse direction by the cam. In this way, an airflow pathway, described in further detail below, is created which extends around the rupturing member 114. The mouthpiece portion 404 may comprise a filter material, such as cellulose acetate tow.

Figure 5:
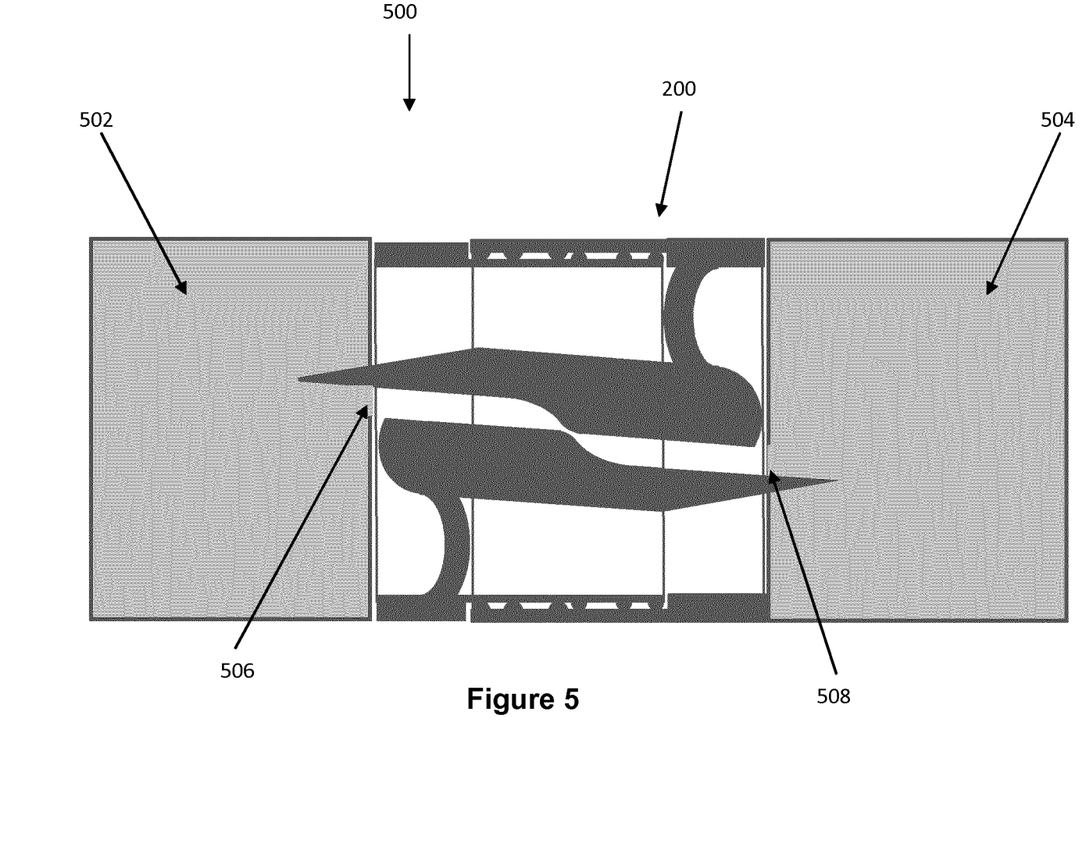
FIG. 5 shows a cross-sectional view of an alternative container according to the present invention.

FIG. 5 shows a cross-sectional view of an alternative container 500 comprising a rupturing system 200 as described above. The container 500 comprises a first sealed compartment 502 comprising a volatile liquid nicotine source, a rupturing system 200, and a second sealed compartment 504 comprising a volatile delivery enhancing compound. As will be appreciated, the volatile liquid nicotine source may be provided in the second compartment 504, the volatile delivery enhancing compound being provided in the first compartment 502. Similarly, to the container shown in FIG. 5, the rupturing system 200 is shown in the second position. The rupturing member 114 has pierced and torn the frangible barrier of the first sealed compartment to form hole 506, and the rupturing portion 204 has pierced and torn the frangible barrier of the second sealed compartment 504 to form hole 508. The second compartment 504 comprises a tubular porous element (not shown) on which the volatile delivery enhancing compound is sorbed. The longitudinal length of the tubular porous element is less than the longitudinal length of the compartment. The tubular porous portion is positioned at the upstream end.

Figure 6:
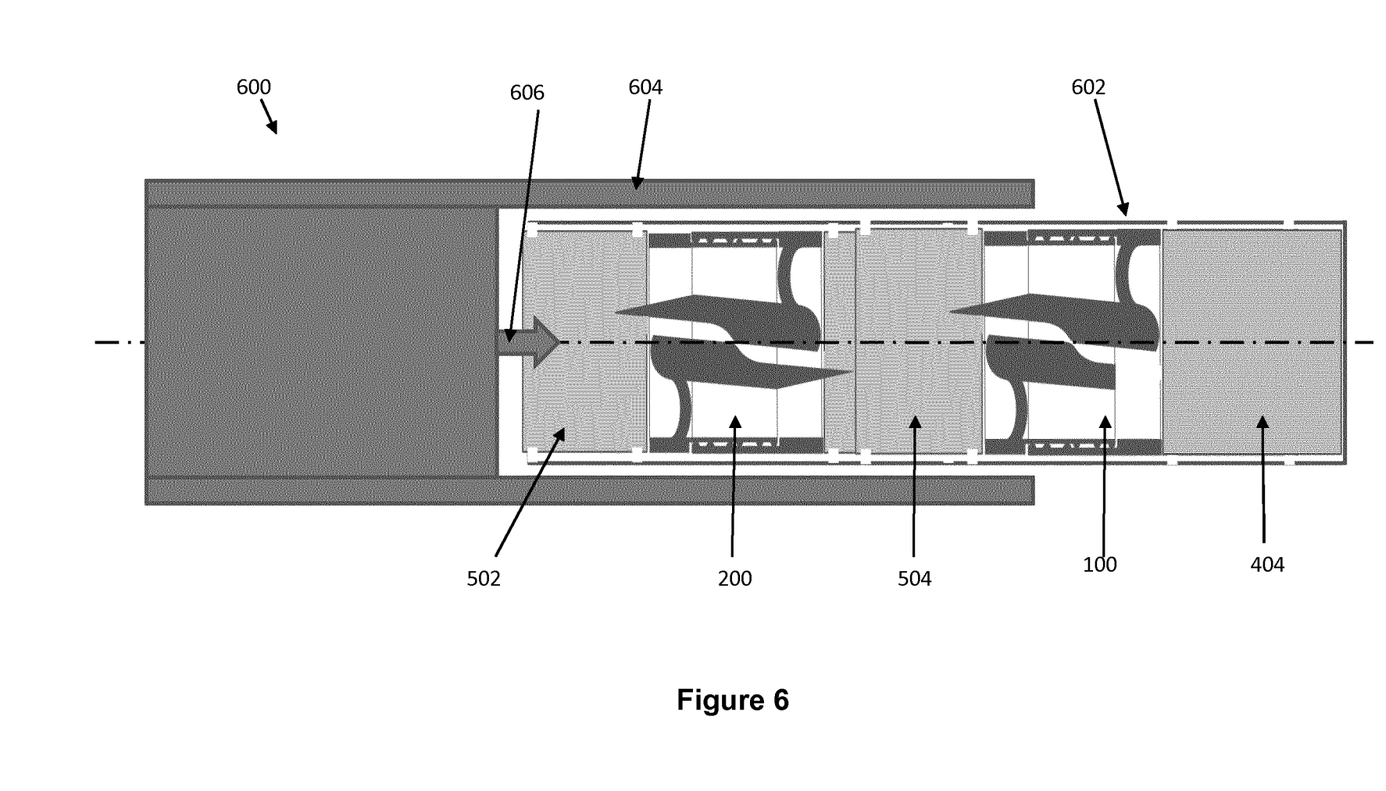
FIG. 6 shows a cross-sectional view of an aerosol-generating system according to the present invention.

FIG. 6 shows a cross-sectional view of an aerosol-generating system 600. The system 600 comprises a container 602 and an aerosol-generating device 604. In this example, the container 602 comprises a first compartment 502, a first rupturing system 200, a second compartment 504, a second rupturing system 100, and a mouthpiece 404. As will be appreciated, the container 602 is a combination of the container 400 and the container 500 shown in FIGS. 4 and 5 respectively, and so for brevity will not be described again here. The aerosol-generating device 604 comprises an outer housing having an elongate cylindrical cavity configured to receive the container 602. The longitudinal length of the cavity is less than the length of the container such that the proximal, or downstream, end of the container 602 protrudes from the cavity.

The device 604 further comprises a piercing member 606. The piercing member is positioned centrally within the cavity of the aerosol-generating device and extends along the longitudinal axis of the cavity. At one end, the piercing member comprises a piercing portion in the form of a cone having a circular base. The piercing member further comprises a shaft portion. As can be seen, when the container is received within the aerosol-generating device, the piercing member is configured to pierce the upstream frangible barrier of the first compartment 502.

Air inlets (not shown) are provided at the upstream end of the aerosol-generating device 604. Air outlets (not shown) are provided at the proximal, downstream, mouthpiece end of the container 602.

In use, the user applies a longitudinal compressive force to the container to move the rupturing systems 200 and 100 to the second position thereby rupturing all of the frangible barriers except for the upstream frangible barrier of the first compartment. The container 602 is then inserted into the device 604. The piercing portion 606 breaks the upstream frangible barrier of the first compartment 502 and creates a hole in the seal having a diameter approximately equal to the maximum diameter of the piercing portion. The maximum diameter of the piercing portion is the diameter of the base circle of the cone which forms the piercing portion.

As such, an airflow pathway is created extending from the air inlet (not shown) around the shaft of the piercing member 606, through the first compartment 502, through the rupturing system 200, through the second compartment 504, through the second rupturing system 100, exiting through the mouthpiece 404.

The invention claimed is:

1. A rupturing system, comprising:
  a first hollow tube and a second hollow tube, the first hollow tube and the second hollow tube each comprising an external surface and an internal surface, the first hollow tube extending longitudinally between a first tube proximal end transverse cross section and a first tube distal end transverse cross section, the second hollow tube extending longitudinally between a second tube proximal end transverse cross section and a second tube distal end transverse cross section, the first hollow tube and the second hollow tube being arranged in operational engagement such that, in the operationally engaged first hollow tube and second hollow tube, the first tube distal end transverse cross section is longitudinally positioned between the second tube proximal end transverse cross section and the second tube distal end transverse cross section, and the second tube proximal end transverse cross section is longitudinally positioned between the first tube proximal end transverse cross section and the first tube distal end transverse cross section, and such that the operationally engaged first hollow tube and second hollow tube extend longitudinally between the first tube proximal end transverse cross-section and the second tube distal end transverse cross-section, the operationally engaged first hollow tube and second hollow tube defining a volume longitudinally delimited by the first tube proximal end transverse cross-section and the second tube distal end transverse cross-section and transversely delimited by the internal surface of the first hollow tube and the internal surface of the second hollow tube,
  wherein the first hollow tube and the second hollow tube are movable relative to each other along a first motion path from a first position to a second position, such that the defined volume is larger in the first position than in the second position,
  wherein the first hollow tube comprises a first rupturing member, disposed at least partially inside the first hollow tube, such that in the first position, the first rupturing member is contained completely in the defined volume, and
  wherein in the second position, the first rupturing member at least partially protrudes from the defined volume to rupture a container.

2. The rupturing system according to claim 1, a guide member of the second hollow tube being a second rupturing member, wherein in the second position, the second rupturing member at least partially protrudes from the defined volume into a second container.

3. An aerosol-generating system, comprising:
  a first container comprising at least one aerosol-generating substrate; and
  a rupturing system, comprising a first hallow tube and a second hollow tube, the first hollow tube and the second hollow tube each comprising an external surface and an internal surface, the first hollow tube extending longitudinally between a first tube proximal end transverse cross section and a first tube distal end transverse cross section, the second hollow tube extending longitudinally between a second tube proximal end transverse cross section and a second tube distal end transverse cross section, the first hollow tube and the second hollow tube being arranged in operational engagement such that, in the operationally engaged first hollow tube and second hollow tube, the first tube distal end transverse cross section is longitudinally positioned between the second tube proximal end transverse cross section and the second tube distal end transverse cross section, and the second tube proximal end transverse cross section is longitudinally positioned between the first tube proximal end transverse cross section and the first tube distal end transverse cross section, and such that the operationally engaged first hollow tube and second hollow tube extend longitudinally between the first tube proximal end transverse cross-section and the second tube distal end transverse cross-section, the operationally engaged first hollow tube and second hollow tube defining a volume longitudinally delimited by the first tube proximal end transverse cross-section and the second tube distal end transverse cross-section and transversely delimited by the internal surface of the first hollow tube and the internal surface of the second hollow tube,
  wherein the first hollow tube and the second hollow tube are movable relative to each other along a first motion path from a first position to a second position, such that the defined volume is larger in the first position than in the second position,
  wherein the first hollow tube comprises a first rupturing member, disposed at least partially inside the first hollow tube, such that in the first position, the first rupturing member is contained completely in the defined volume, and
  wherein in the second position, the first rupturing member at least partially protrudes from the defined volume to rupture the first container comprising the at least one aerosol-generating substrate.

4. The aerosol-generating system according to claim 3, wherein the first rupturing member comprises a distal end comprising a rupturing portion and a proximal end, and wherein the first rupturing member is coupled to the first tube at the proximal end such that during movement of the first tube along the first motion path, the rupturing portion describes a second motion path that is at least partially not parallel to the first motion path.

5. The aerosol-generating system according to claim 4, wherein the second hollow tube comprises a guide member configured to guide the rupturing portion of the first rupturing member along the second motion path.

6. The aerosol-generating system according to claim 5, wherein the guide member comprises a cam surface, and
wherein the first rupturing member further comprises a cam follower surface, such that during relative movement of the first hollow tube and the second hollow tube from the first position to the second position along the first motion path, the cam follower surface of the first rupturing member engages with the cam surface of the guide member to guide the rupturing portion of the first rupturing member along the second motion path.

7. The aerosol-generating system according to claim 3, a guide member of the second hollow tube being a second rupturing member, wherein in the second position, the second rupturing member at least partially protrudes from the defined volume into a second container.

8. The aerosol-generating system according to claim 7,
wherein the second rupturing member comprises a distal end comprising a rupturing portion and a proximal end, and
wherein the second rupturing member is connected to the second tube at the proximal end such that during movement of the second tube along the first motion path, the rupturing portion describes a third motion path that is at least partially not parallel to the first motion path.

9. The aerosol-generating system according to claim 3, wherein the first rupturing member is coupled to the first tube by a resilient member.

10. The aerosol-generating system according to claim 3, wherein an external surface of the first hollow tube is configured to slide adjacent an internal surface of the second hollow tube.

11. The aerosol-generating system according to claim 10, wherein the external surface of the first hollow tube and the internal surface of the second hollow tube each comprise resilient protrusions configured to cooperate to retain the system in the first position until a longitudinal compressive force is applied to the system.

12. The aerosol-generating system according to claim 10, wherein the external surface of the first hollow tube and the internal surface of the second hollow tube each comprise resilient protrusions configured to cooperate to retain the system in the second position.

13. The aerosol-generating system according to claim 10, wherein the first hollow tube comprises a shoulder, the system further comprising a removable tab disposed adjacent the shoulder and adjacent the end face of the second hollow tube and being configured to prevent the first hollow tube and second hollow tube from moving from the first position to the second position.

14. The aerosol-generating system according to claim 3,
wherein the first container further comprises a first closed compartment comprising the aerosol-generating substrate, the first closed compartment having at least one frangible barrier, and
wherein the at least one frangible barrier defines a border of the defined volume.

15. The aerosol-generating system according to claim 14, further comprising:
at least one further rupturing system comprising a further first tube and a further second tube; and
a mouthpiece element directly coupled to one of the further first tube or the further second tube of the at least one further rupturing system.

16. The aerosol-generating system according to claim 3, further comprising at least one heater configured to heat the aerosol-generating substrate to form an aerosol.

* * * * *